United States Patent
Taimoorazy

(10) Patent No.: US 7,055,524 B1
(45) Date of Patent: Jun. 6, 2006

(54) AIRWAY MANAGEMENT DEVICE

(76) Inventor: Benjamin Taimoorazy, 7 Smokey Ct., Bloomington, IL (US) 61704

( * ) Notice: Subject to any disclaimer, the term of this patent is extended or adjusted under 35 U.S.C. 154(b) by 131 days.

(21) Appl. No.: 10/256,684

(22) Filed: Sep. 27, 2002

(51) Int. Cl.
*A61G 15/00* (2006.01)
*A61F 5/37* (2006.01)
*A61F 15/00* (2006.01)

(52) U.S. Cl. .................. 128/845; 128/870; 602/32

(58) Field of Classification Search .......... 128/95.1, 128/97.1, 845, 846, 848, 857, 869, 870, DIG. 23; 601/41–44; 602/18, 902, 32, 33; 297/391; 5/631, 632, 652, 636, 637; 2/468, 10; 27/25.1, 27/845

See application file for complete search history.

(56) References Cited

U.S. PATENT DOCUMENTS

| | | | | |
|---|---|---|---|---|
| 837,612 | A * | 12/1906 | Davis | 27/25.1 |
| 1,441,817 | A * | 1/1923 | McCullough | 27/25.1 |
| 2,088,207 | A * | 7/1937 | Kaiser | 297/392 |
| 2,210,113 | A * | 8/1940 | Davis | 27/25.1 |
| 2,238,931 | A * | 4/1941 | De Laney | 27/21.1 |
| 2,576,871 | A * | 11/1951 | Wright | 27/25.1 |
| 3,283,755 | A * | 11/1966 | Harden | 601/143 |
| 3,306,284 | A * | 2/1967 | McKinley | 602/18 |
| 3,596,655 | A * | 8/1971 | Corcoran | 602/32 |
| 4,220,147 | A * | 9/1980 | Allen, III | 602/36 |
| 4,266,759 | A * | 5/1981 | Liebman | 5/632 |
| 4,565,408 | A * | 1/1986 | Palley | 297/393 |
| 4,643,174 | A * | 2/1987 | Horiuchi | 602/18 |
| 5,297,540 | A * | 3/1994 | Kaiser et al. | 601/27 |
| 5,487,395 | A * | 1/1996 | Strowe | 128/878 |
| 5,682,632 | A | 11/1997 | Cotroneo | |
| 6,000,401 | A | 12/1999 | Herrick | |
| 6,171,314 | B1 | 1/2001 | Rotramel | |
| 6,899,690 | B1 * | 5/2005 | Saunders et al. | 602/36 |

* cited by examiner

*Primary Examiner*—Teena Mitchell
(74) *Attorney, Agent, or Firm*—Patzik, Frank & Samotny Ltd.

(57) ABSTRACT

An apparatus for maintaining airway passages open that includes a base and a horizontal bar member slidably connected to a U-shaped member attached to the base. A pair of posts having padded heads or end members for contacting the mandibular angle of a jaw of a person are rotationally attached to a bolt that extends from the base adjacent the end of the U-shaped member and a bolt that extends from the base proximate the end of the horizontal bar member. Rotation of the posts about the bolts allows for the adjustment of the height of the posts. The posts and bolts may also be pivoted to position the padded end members to correctly contact the jaw of the person. Sliding the horizontal bar member in relation to the U-shaped member allows for the distance between posts to be adjusted to accommodate the different sized heads of different people.

14 Claims, 2 Drawing Sheets

AIRWAY MANAGEMENT DEVICE

FIELD OF THE INVENTION

This invention relates in general to an apparatus for maintaining open airways or air passages to ensure that people continue to breath properly while under anesthesia, and more particularly, to an apparatus for maintaining airways open during medical procedures that may be adjustable for use with a wide variety of people, and still more particularly, to an apparatus having a pair of adjustable posts for pressing against the jaws of people to maintain their airways open by simulating a jaw thrust during anesthesia.

BACKGROUND OF THE INVENTION

During medical procedures such as surgeries, it is critical that the patient's airway remains open so that the patient properly breathes during the procedure. Keeping the airway open is especially important in procedures where anesthesia is used as anesthesia causes the muscles to relax and renders the patient in a state where he may be unable to wake up if the airway passage is blocked.

One known way for ensuring that the airway remains open during medical procedures is to have the anesthesiologist monitor the patient and hold the patient's head in the proper position. If the airway becomes blocked, the anesthesiologist can perform a chin lift maneuver by tilting and holding the patients chin in a backward fashion, or a "jaw thrust" by pushing the patient's jaw upward to open the airway. While these maneuvers work, the anesthesiologist must continue to monitor and/or hold the patient's head position throughout the procedure. Thus, the anesthesiologist will be unable to perform other tasks that may be needed during the procedure. Furthermore, during long procedures, the anesthesiologist may become fatigued from having to hold the patient's head in a particular position for an extended period of time.

Another known way to maintain airways open is to have a medical professional intubate the patient by inserting an endotracheal tube through the patient's mouth. However, endotracheal tubes can cause irritation of the throat and/or vocal chords that may lead to additional surgeries or problems.

Additionally, it is also known to use a headrest or apparatus that utilizes two or more fixed posts to try and maintain airways open. However, the known devices are not adjustable, therefore, depending on the size and shape of a patient's head and neck, the posts may not be properly positioned against the patient's jaw to adequately open or maintain openness of the airway. Furthermore, a patient will often experience varying depths of anesthesia, whereby more jaw thrust will be required as the patient goes into deeper depths of anesthesia. Thus, the anesthesiologist must continually monitor the status of the patients airway when using the prior devices.

Therefore, there is a need to produce an airway management device that is adjustable to ensure that the device is correctly situated against the jaw of a patient to ensure that the patient's airways remain open during surgical procedures, while being economical and easy to manufacture and install.

SUMMARY OF THE INVENTION

The present invention is an innovative improvement over the prior devices and ways to maintain a person's airway open in that the posts of the device are adjustable as to length and angle with respect to the base to ensure that they properly contact the mandibular angle of the person's jaw. In particular, the airway management device of the present invention includes a pair of spaced apart posts separated by a horizontal bar member. A removable padded head is attached to the end of each post at an angle relative to the base for contacting the jaw of the patient. The padded head can be mounted to each post so that the angle of the padded head to the post can be varied.

In operation, the horizontal bar member and posts are adjustable to allow for a medical professional to ensure that the posts press against the mandibular angle of the patient's jaw to ensure that the airways remain open during medical procedures. In particular, the posts, which are slightly angled toward the top of the patients head and pivotally attached to the base or horizontal bar, may be rotated in a clockwise or counter-clockwise direction to respectively lower or raise the height of the posts. By adjusting the height of the posts and pivoting the posts, a medical professional can correctly position and align the posts to contact the mandibular angle of the persons jaw in such a way as to simulate a "jaw thrust" in order to maintain the airways open. Additionally, the horizontal bar member may be adjusted to vary the distance between the posts and therefore accommodate heads of varying sizes.

It is therefore an object of the present invention to provide a new and improved airway management device that ensures that a person's airway remains open during anesthesia.

Another object of the present invention is to provide an airway management device that provides posts that may be adjusted and pivoted to properly contact a persons jaw to ensure that the persons airway remains open.

A further object of the present invention is to provide an airway management device that may be adjustable to compensate for different depths of anesthesia during medical procedures.

A yet further object of the present invention is to provide an airway management device that is adjustable to allow it to be used on a variety of different people.

Other objects, features and advantages of the invention will be apparent from the following detailed disclosure, taken in conjunction with the accompanying sheets of drawings, wherein like reference numerals refer to like parts.

DETAILED DESCRIPTION OF THE INVENTION

Figure 1:
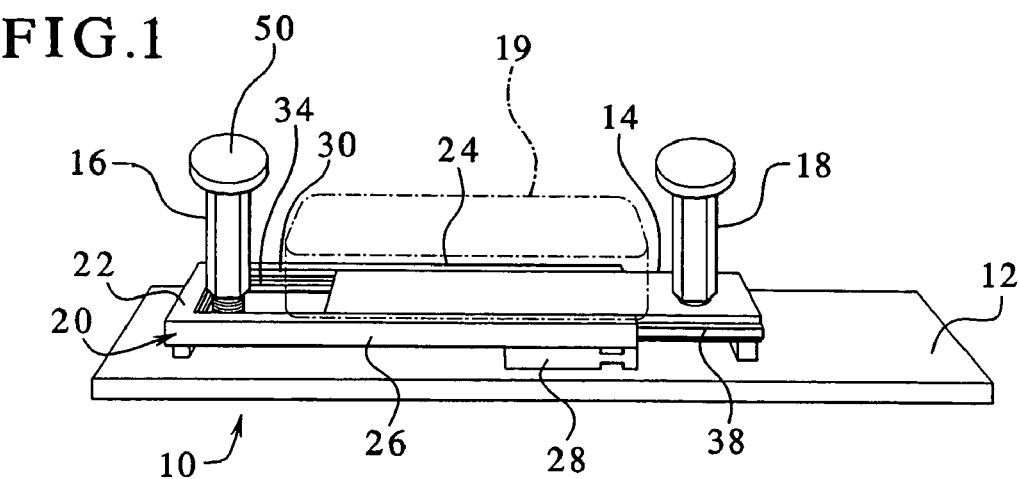
FIG. 1 is a perspective view of an embodiment of the airway management device showing the posts in their lowest position and the horizontal bar member substantially within the U-shaped member.

While this invention is susceptible of embodiment in many different forms, there is shown in the drawings and will herein be described in detail several specific embodiments, with the understanding that the present disclosure is to be considered merely an exemplification of the principles of the invention and the application is limited only to the appended claims.

Referring now to the drawings, and particularly to FIGS. 1 through 5, there is shown a preferred embodiment of the present invention. The airway management device, generally designated by the number 10, is shown as having a base 12, a horizontal bar member 14 and a pair of spaced apart posts 16,18. The base, horizontal bar member and posts may be made from a variety of material including, but not limited to wood, plastic, or metal.

Figure 5:
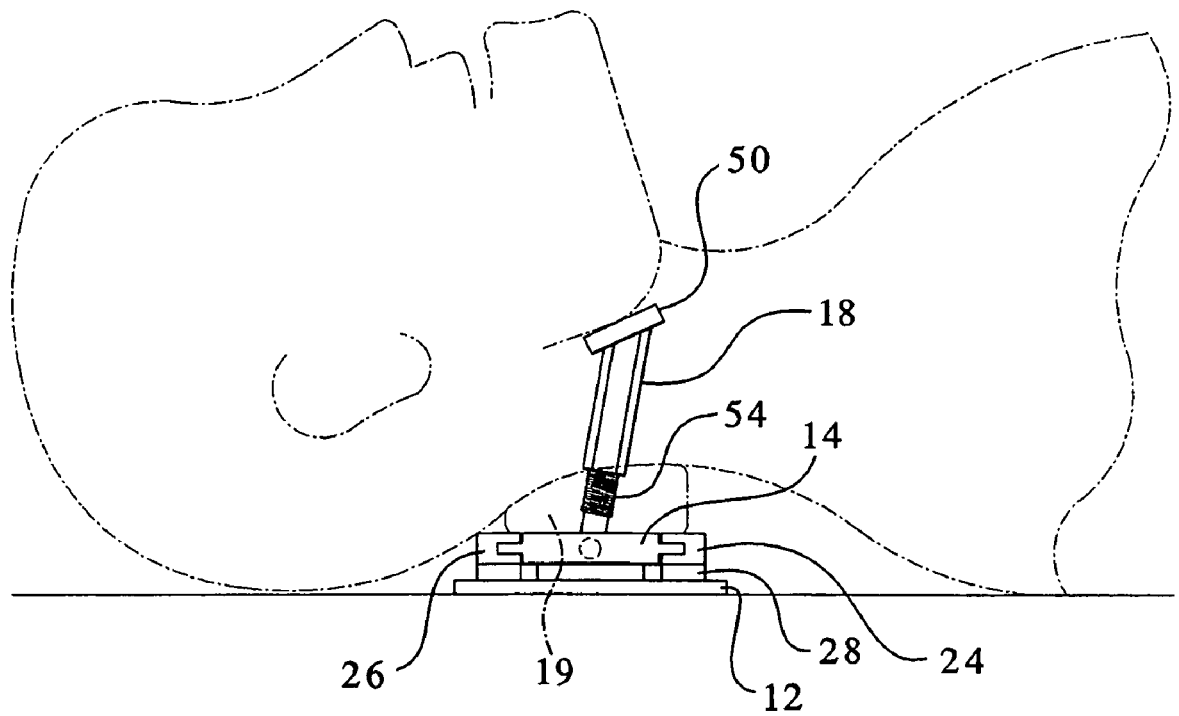
FIG. 5 is a side elevational view illustrating the airway management device being positioned beneath the head of a patient with a post extended and pivoted to contact the jaw of the patient.

The base 12 of the airway management device 10 is sized such that it may be comfortably placed underneath the neck or the head, as shown in FIG. 5. While a rectangular base is shown, it is appreciated that the base may be of any of a variety of shapes and sizes and not depart from the scope of the invention. It is further appreciated that if the device is placed under the head of a patient, a pad 19 (shown in phantom in FIGS. 1–3 and 5) may be placed on top of the horizontal bar to provide a comfortable surface for the head to rest upon. The pad is preferably removably attached to the horizontal bar in a known way, such as, but not limited to, with Velcro® hook and loop type fasteners, to allow for the pad to be replaced for subsequent procedures.

Attached to the base 12 is a U-shaped member 20 having an end 22 and a pair of side member 24, 26. The U-shaped member is preferably spaced apart from the base using a plurality of spacers 28. While the U-shaped member may be attached to the base using any known attaching means such as, but not limited to, adhesives, it is appreciated that the U-shaped member may be integral with the base.

The insides 30 of the side members 24, 26 include grooves 34 that extends along the axial length of the side members for accepting flanges 38 extending along the sides of the horizontal bar member 14. The frictional interaction between the flanges and grooves retains the horizontal bar member within the U-shaped member while allowing for axial movement of the horizontal bar member. Retention could also be achieved by using a series of spring-loaded bearing which roll into a series of circular holes as the bar member 14 is extended or retracted. Furthermore, while flanges and a U-shaped member having grooves are shown and disclosed, it is appreciated that the horizontal bar member may be slidably attached to the base using other known means including, but not limited to, a slot or groove on the base for accepting a flange or other retaining member associated with the horizontal bar member.

Figure 2:
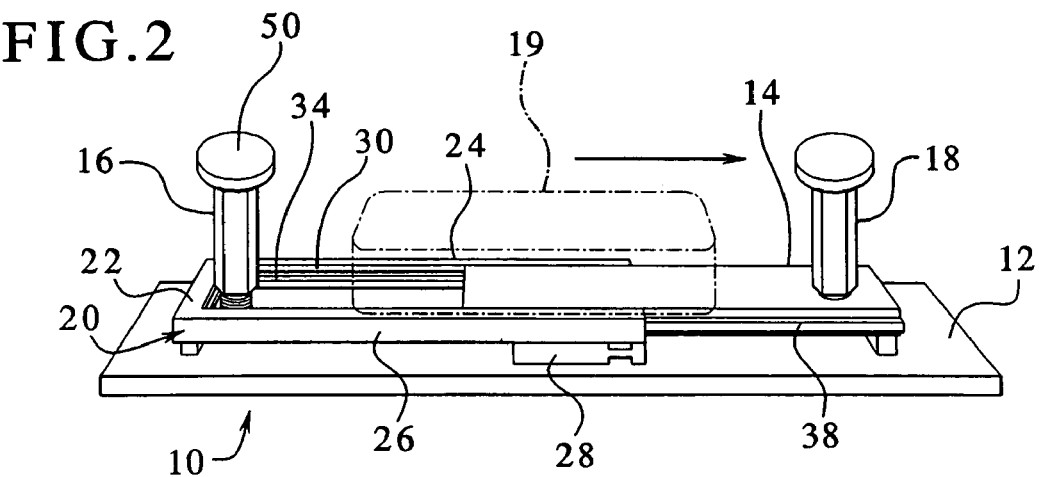
FIG. 2 is a perspective view of the airway management device of FIG. 1 showing the horizontal bar member partially pulled from the U-shaped member to provide a greater distance between the two posts.
Figure 3:
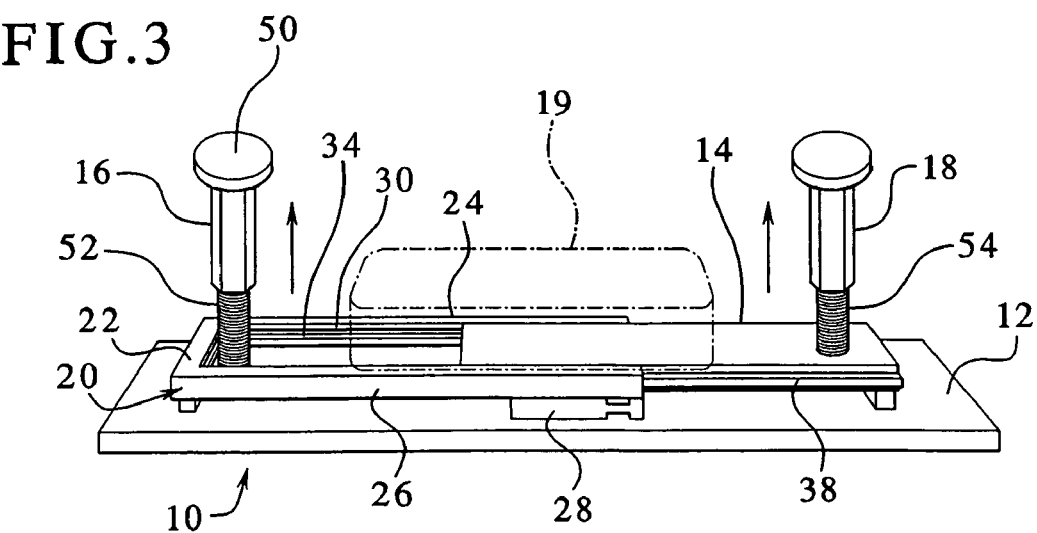
FIG. 3 is a perspective view of the airway management device of FIG. 2 showing the posts in their highest position.

Referring to FIGS. 1 to 3, the device 10 preferably includes a bolt 52 that extends from the base 12 adjacent the end of the U-shaped member 20 and a bolt 54 that extends from the end of the horizontal bar member 14 for attaching the posts 16,18. In order to accommodate the bolts 52,54, each of the posts 16,18 preferably includes a threaded cavity or bore (not shown). While a bolt and threaded cavity are shown and disclosed, it is appreciated that the posts may be vertically adjusted by extending or retracting the posts using other known means including, but not limited to, a telescoping arrangement or pins and clips for insertion into one of a plurality of holes on the bolts and/or posts. In order to properly and effectively contact the jaw, the posts 16,18 preferably are attached to the base 12 or horizontal bar member 14 such that the posts are slightly angled from the vertical, as shown in FIGS. 1 through 3.

Figure 4:
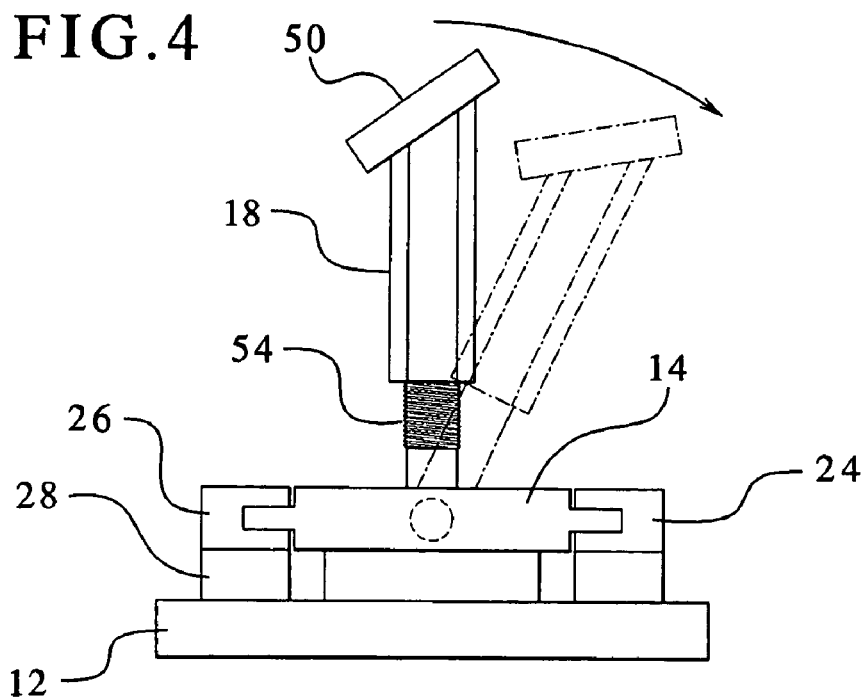
FIG. 4 is a side elevational view of the airway management device of FIG. 1 showing the movement of the post about a pivot point on the horizontal bar member in phantom.

As shown in FIGS. 4 and 5, to provide the optimum angle for the maximum number of different patients, the posts are preferably pivotally, yet securely, attached to the base or horizontal bar member in a known way, such as by using ball and socket joints, to allow the posts to rotate or pivot in a direction substantially perpendicular to the longitudinal direction of the base so as to contact the jaw when the device is placed beneath the neck. It is appreciated that the joint could be ratcheted so as to hold the post in a number of different angular positions. Alternatively, the friction of the ball in the socket could hold the post at a desired angle.

The top ends of the posts are preferably angled to embrace the angle of the jaw. A padded head 50 is also preferably attached to the top end of each of the posts 16,18 to provide a comfortable contact point for pressing against the jaw. The padded head is preferably removably attached to the end of the posts in a known way, such as with Velcro, to permit the pads to be removed and replaced for subsequent procedures. The padded head can also be attached to the posts in such a way that the angle of the padded head relative to the post can vary so as to better fit the patient and provide the most comfortable fit.

In operation, the airway management device 10 is placed on an operating table or other flat surface. The horizontal bar member 14 is slid axially within the U-shaped member 20 until the posts 16,18 are spaced apart the proper distance to accommodate the head. The top portion of the posts 16,18 are then rotated either clockwise or counter-clockwise and pivoted relative to the base until the padded heads 50 of the posts 16,18 contact the mandibular angle of the jaw to maintain a jaw thrust so as to keep the airways open. It is appreciated that while the angle of the posts relative to the base will vary depending on the particular patient, the typical angle of the posts will be in the range of about 70 to 75 degrees. It is further appreciated that the posts may be further adjusted during the medical procedure to accommodate any movement of the jaw due to varying depths of anesthesia experienced. The device 10 may be used for other patients by replacing the pad and padded heads and by adjusting the horizontal bar member 14 and posts 16,18 to accommodate different sized and shaped heads.

It will be understood that modifications and variations may be effected without departing from the scope of the novel concepts of the present invention, but it is understood that this application is limited only by the scope of the appended claims.

The invention claimed is:

1. An airway management device for contacting the jaw of a person comprising:
   a base;
   a horizontal bar member;
   a first post attached to the horizontal bar member for contacting the jaw of the person;
   means to adjust the height of the first post;
   a second post attached to the base for contacting the jaw of the person;
   means to adjust the height of the second post; and
   means to adjust the distance between the first and second posts comprising means to slidably move the horizontal bar member relative to the base.

2. The airway management device of claim 1 wherein the means to slidably move the horizontal bar member comprises a U-shaped member comprising an end and a pair of leg members having interior sides, the interior sides comprising a groove and the horizontal bar member comprises a flange, wherein the horizontal bar member is inserted into the U-shaped member such that the flange is slidably attached within the groove to allow the horizontal bar member to move axially.

3. The airway management device of claim 1 wherein the first and second posts are slightly angled from the vertical.

4. The airway management device of claim 1 wherein the first and second posts are pivotally attached to said base to allow the posts to be positioned at multiple angles.

5. The airway management device of claim 1 wherein the first and second posts include a padded head.

6. The airway management device of claim 5 wherein the padded heads of the first post and second post are positioned at an angle relative to the base.

7. The airway management device of claim 1 wherein the means to adjust the height of the first post comprises a threaded bore within the first post and a first bolt extending from the horizontal bar member, wherein the post may be rotated to adjust the position of the first post along the first bolt.

8. The airway management device of claim 1 wherein the means to adjust the height of the second post comprises a threaded bore within the second post and a second bolt extending from the base, wherein the second post may be rotated to adjust the position of the second post along the second bolt.

9. The airway management device of claim 1 which further includes a pad removably attached to the horizontal bar member.

10. A device for contacting the mandibular angle of the jaw of a person to maintain the person's air passages open while under anesthesia comprising:
   a base;
   a horizontal bar member;
   a first post having an angled surface for contacting the mandibular angle of the jaw, wherein the first post is pivotally attached to the horizontal bar member to allow the first post to be positioned at multiple angles relative to the base;
   means to adjust the height of the first post;
   a second post having an angled surface for contacting the mandibular angle of the jaw, wherein the second post is pivotally attached to the base to allow the second post to be positioned at multiple angles relative to the base;
   means to adjust the height of the second post; and
   means to adjust the distance between the first and second posts comprising means to slidably move the horizontal bar member relative to the base.

11. The device of claim 10 which further includes a first padded head attached to the angled surface of the first post and a second padded head attached to the angled surface of the second post.

12. The device of claim 11 wherein the first and second padded heads are removably attached to the first and second posts.

13. The device of claim 10 wherein the first and second posts are slightly angled from the vertical.

14. The device of claim 10 wherein the means to adjust the distance between the first and second post comprises a U-shaped member comprising an end and a pair of leg members having interior sides, the interior sides comprising a groove and the horizontal bar member comprises a flange, wherein the horizontal bar member is inserted into the U-shaped member such that the flange is slidably attached within the groove to allow the horizontal bar member to move axially.

* * * * *